United States Patent
Quinn et al.

[11] Patent Number: 6,149,816
[45] Date of Patent: Nov. 21, 2000

[54] CHEMICAL ANALYSES

[75] Inventors: Hubert M. Quinn, Brighton; John E. Brann, III, Boylston, both of Mass.

[73] Assignee: Cohesive Technologies, Inc., Franklin, Mass.

[21] Appl. No.: 09/476,257

[22] Filed: Jan. 3, 2000

Related U.S. Application Data

[62] Division of application No. 08/974,336, Nov. 19, 1997.

[51] Int. Cl.$^7$ .................................................. B01D 15/08
[52] U.S. Cl. ........................ 210/635; 210/656; 210/198.2
[58] Field of Search ................................... 210/635, 656, 210/659, 198.2, 502.1

[56] References Cited

U.S. PATENT DOCUMENTS

| | | | |
|---|---|---|---|
| 3,493,497 | 2/1970 | Pretorius et al. | 210/31 |
| 4,208,284 | 6/1980 | Pretorius | 210/198.2 |
| 4,389,385 | 6/1983 | Ramsay | 210/198.2 |
| 4,512,897 | 4/1985 | Crowder | 210/198.2 |
| 4,970,002 | 11/1990 | Tanimura et al. | 210/659 |
| 5,015,576 | 5/1991 | Nilsson | 210/656 |
| 5,019,270 | 5/1991 | Afeyan et al. | 210/198.2 |
| 5,164,090 | 11/1992 | Hirth | 210/198.2 |
| 5,228,989 | 7/1991 | Afeyan et al. | 210/198.2 |
| 5,256,298 | 10/1993 | Powell | 210/660 |
| 5,268,097 | 12/1993 | Girot | 210/198.2 |
| 5,328,603 | 7/1994 | Velander | 210/198.2 |
| 5,384,042 | 1/1995 | Afeyan et al. | 210/198.2 |
| 5,387,347 | 2/1995 | Rothchild et al. | 210/659 |
| 5,401,415 | 3/1995 | Rauh | 210/198.2 |
| 5,503,933 | 4/1996 | Afeyan | 210/198.2 |
| 5,772,874 | 6/1998 | Quinn | 210/198.2 |
| 5,795,467 | 8/1998 | Quinn | 210/198.2 |

FOREIGN PATENT DOCUMENTS

| | | | |
|---|---|---|---|
| 1452896 | 10/1976 | United Kingdom | 210/198.2 |
| WO9320499 | 10/1993 | WIPO | 210/198.2 |

OTHER PUBLICATIONS

C. Giddings, Advances in the Theory of Plate Height in Gas Chromatography, *Analytical Chemistry*, vol. 35, No. 4, Apr. 1963, pp. 439–448.

Sir G. Taylor, Fluid Flow in Regions Bounded by Porous Surfaces, *Proc. Royal Soc. of London*, vol. 234A, 1956, 456–475.

W. Kopaciewicz et. al., High Velocity Reversed Phase Chromatography of Proteins and Peptides; Use of Conventional C18, 300Å, 15 μm Particles, *J. Chromatog*. A, 690, 1995, 9–19.

C. Giddings, et. al., Plate Height in Gas Chromatography, *Analytical Chemistry*, vol. 32, No. 7, Jun. 1960, pp. 867–870.

(List continued on next page.)

*Primary Examiner*—Ernest G. Therkorn
*Attorney, Agent, or Firm*—Schiller & Associates

[57] ABSTRACT

A system for separating compounds of relatively low molecular weight substantially not greater than about one kilodalton from compounds having relatively high molecular weights substantially an order of magnitude greater or more than the low molecular weight compounds in a liquid mixture. The system includes a chromatographic column packed with uniformly distributed rigid, solid, porous particles having chromatographically active, hydrophobic surfaces, average diameters of not less than about 30 μm, and average pore diameters sufficiently small to substantially exclude introduction of the compounds of relatively high molecular weight into the pores. The mixture is pumped through the interstitial volume between the particles at a reduced velocity greater than about 5,000, until a band of the high molecular weight compounds exits the column. The low molecular weight compounds are then eluted and are recovered separately from the relatively high molecular weight compounds. Spectrographic identification of the recovered low molecular weight compounds can then be made, preferably by ultraviolet absorption or by mass spectrograph.

10 Claims, 3 Drawing Sheets

OTHER PUBLICATIONS

V. Pretorius and T. Smuts, Turbulent Flow Chromatography: a New Approach to Faster Analysis, *Analytical Chemistry*, vol. 38, No. 2, Feb. 1966, pp. 274–280).

D.S. Horne et. al., A Comparison of Mobile–Phase Peak Dispersion in Gas and Liquid Chromatography, *Sep. Science*, 1(5), 531–554 (1966).

S.H. Sumpter, et. al., Enhanced Radial Dispersion In Open Tubular Column Chromatography, *J. Microcol.*, Sep. 3, 91–113, (1991).

H. Bauer, Open–Tubular Liquid Chromatography under Turbulent and Secondary Flow Conditions, *Chromatographia*, vol. 27, No. 5/6, 238–242, (Mar. 1989).

R. Tijssen, Liquid Chromatography in Helically Coiled Open Tubular Columns, *Sep. Science and Tech.*, 13(8), 681–722 (1978).

M. Martin et. al., Influence of Retention on Band Broadening in Turbulent Flow Liquid and Gas Chromatography., *Anal. Chem.*, 54, 1533–1540 (1982).

D. Dewaele et. al., Some L.C.Experiments with Capillary Columns, *J. High Res. Chromatog. and Chromatog. Commun.*, 1, 174–176 (Sep. 1978).

K. Hofmann et. al., Mass Transfer in Ideal and Geometrically Deformed Open Tubes, III. Deformed Metal and Plastic Tubes, *J. Chromatog.* 199, 3, (1980).

Giddings, Reduced Plate Height Equation: a Common Link Between Chromatographic Methods; *Journal of Chromatography*, 13, 301–304 (1964).

Guichon, *Fundamentals of Preparative and Non–Linear Chromatography*, Academic Press, 174–176, (1994).

Snyder, et al. *Introduction to Modern Liquid Chromatography*, John Wiley & Sons, 173–176; 210–216; 234–240, 484–486, 493, 595–597, 603–607 (1979).

Aris, On the Dispersion of a Solute in a Fluid Flowing Through a Tube, *Proc. Roy. Soc.*, A235, 67–77, (1956).

Aris, On the Dispersion of a Solute by Diffusion, Convection and Exchange Between Phases, *Proc. Roy. Soc.*, A252, 538–550, (1959).

CHEMICAL ANALYSES

This application is a division of allowed application Ser. No. 08/974,336, filed Nov. 19, 1997.

This application relates to chemical analyses, and more particularly methods and apparatus for analysis of mixtures of relatively low molecular weight organic compounds (e.g. less than about a few kilodaltons) with relatively high molecular weight (e.g. one or more orders of magnitude larger than the low molecular weight (mw) compounds.

For example, in assessing the development, selection and optimization of proposed new pharmaceuticals, it is important to obtain metabolic, pharmicokinetic, stability and toxicological data on the proposed drugs with a minimum of delay. In many instances, the proposed drugs, typically with molecular weights below about a few kilodaltons (kd), are created by combinatorial chemistry which yields such very large numbers of drug candidates. Conventional analytical protocols for such numbers of drug candidates tend to be overwhelmed, being too slow. Such traditional protocols usually require scale-up, extraction, separation and fractionation of complex mixtures, followed by spectroscopic analysis of each individual fraction, so the time constraints imposed by such methods constitute a serious bottleneck in the process of evaluation of the drug candidates.

It has been suggested that inasmuch as metabolites tend to retain most of the substructures of the compounds from which they are derived, metabolic and stability data can be obtained by subjecting a combinatorial or other like complex mixture to forced degradation in vitro or in-vivo metabolic conditions, and then analyzing the treated sample with parallel processing by liquid chromatography and mass spectrometry. Such metabolites obtained from in-vivo or in-vitro processing are usually carried in serum plasma having components that typically exhibit molecular weights of 100 kilodaltons or greater, before spectral analysis of the mixture. Thus, before the several components of such mixtures are analyzed, typically by mass spectrometry and/or HPLC, the mixture usually requires pretreatment, as by precipitation techniques or the like, to remove the high molecular weight proteins to prevent interference with the operation of the mass spectrograph and/or the HPLC.

U.S. Pat. No. 5,164,090, issued Nov. 17, 1992 to W. W. Hirth seeks to avoid pretreatment by flowing whole blood through a chromatographic column specifically formed of porous particles of known internal surface reverse phase resin (ISRP) comprising hydrophobic inner pore surfaces and hydrophilic outer particle surfaces. Mechanical blockage of the system by blood cells is obviated by using particles large enough (e.g. 50 to 100 $\mu$m in diameter) to permit the blood cells, in a non-denaturing solvent, to pass between the particles. The particle pores are small enough the prevent penetration by proteinaceous substances but large enough to be penetrated by free hydrophobic components that are retained proportionately to their affinity for the hydrophobic surfaces in the pores. A hydrophobic solvent is used to elute the hydrophobic materials from the particles for subsequent detection. This system typically employs bed flow rates of about 1 to 1.5 ml/min, which with the maximum bead and column dimensions specified can be shown to yield a reduced velocity of less than 100, a clearly laminar flow through the column and a typical analysis time of about 12 or more minutes.

Recently, as described in International Patent Application WO97/16724 published May 9, 1997 (which is incorporated herein by reference in its entirety and is commonly assigned with the present application), it has been disclosed that, for a liquid mixture being analyzed in a chromatographic column, by judicious selection of particle size (which should be not less than about 30 $\mu$m in diameter), interparticle spacing, particle porosity and particularly the provision of turbulent flow to the mixture, one can dramatically reduce the time required to effect separation of the components of the mixture, particularly for oligonucleotides and similar very large biological molecules. Some of the advantageous aspects of this analytical method are employed in the present invention as will be apparent hereinafter. In this respect, the performance of the analytical method described in the aforesaid International Patent Application WO97/16724 can be described in terms of the relation between the height equivalent to a theoretical plate, H, to the linear velocity, u, of the mobile phase through the column, but is more conveniently described using normalized dimensionless coordinates, the reduced plate height h and the reduced velocity v, respectively in place of H and u. As described in application WO97/16724, at a reduced velocity v greater than about 5000 of the flow of the mobile phase through the column, the flow is turbulent, and the column exhibits behavior markedly different than is predicted by the well-known Van Deemter equation. The reduced velocity, a dimensionless value or coordinate, is defined by the equation, $v=ud_p/D$, where u is the mobile phase velocity of liquid through the column, $d_p$ is the packing particle diameter and D is the diffusion coefficient of the solute in the mobile phase.

A principal object of the present invention is to provide apparatus for and method of rapidly separating the components of a mixture of relatively low molecular weight compounds (typically less than about 1 kd for purposes of the present invention) from compounds having relatively high molecular weights substantially an order of magnitude greater or more than said low molecular weight compounds (i.e. typically 10 kd. or greater for purposes of the present invention). Yet another object of the present invention is to provide improved chromatographic apparatus and methods for extremely fast analytical separation of solutes of widely varying molecular weights.

The present invention therefore is directed to novel methods of and apparatus for separating compounds of a mixture of compounds of at least two widely disparate molecular weights by flowing the mixture through a chromatographic body, preferably in the form of a column packed with a substantially uniformly distributed multiplicity of rigid, solid, porous particles having chromatographically active surfaces, average diameters of not less than about 30 $\mu$m, and average pore diameters sufficiently small to substantially preclude passage of those compounds of relatively high molecular weight into the pores of the particles. The mixture is compelled to flow through the interstitial volume between the particles of the column at a reduced velocity greater than about 5000, i.e. flow turbulently, until a band of the compounds of the relatively higher molecular weight have exited the column. After the relatively high molecular weight compounds (hereinafter referred to as heavyweight compounds) have exited the column, the relatively low molecular weight compounds (hereinafter referred to as lightweight compounds) which have been bound to the chromatographically active surfaces of the particles, are eluted from the column with an eluant liquid. Thereafter, the eluted lightweight compounds are recovered at the exit of the column separately from the relatively heavyweight compounds.

In one embodiment of the present invention, the recovered fraction containing the relatively lightweight compounds is further analyzed by spectrographic analysis, for example by being fed directly into a mass spectrometer or the like. In such case, it is preferred to provide, at the output of the column, an eluant flow rate that will match the acceptable input flow rate to the spectrometer, usually a laminar flow rate.

The foregoing and other objects of the present invention will in part appear obvious, and will in part appear hereinafter. The invention accordingly comprises the apparatus possessing the construction and arrangement of parts exemplified in the following detailed disclosure, and the method comprising the several steps and the relation and order of one or more of the steps with respect to the others, the scope of the application of which will be indicated in the claims.

For a fuller understanding of the nature and objects of the present invention, reference should be had to the following detailed description taken in connection with the drawings wherein like numerals denote like parts.

DETAILED DESCRIPTION OF THE INVENTION

Figure 1:
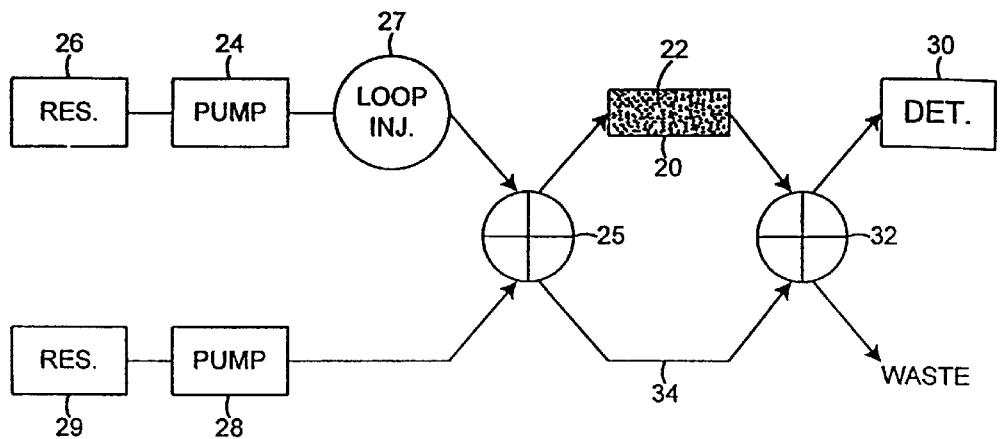
FIG. 1 is a schematic diagram of apparatus embodying the principles of the present invention.

One aspect of the present invention, embodied in the apparatus shown in FIG. 1, includes a chromatographic body 20 formed preferably as a column of a packed multiplicity of rigid, solid particles 22 having substantially uniform mean diameters of greater than about 30 μm. The term "mean diameter" as used herein is intended to mean the average or mean diameter or cross-section dimension of a particle regardless of its configuration, and should not be construed as limited to particles that are necessarily a regularly shaped solids. The particles in the column are formed from substantially incompressible materials, i.e. the time rate of change of the particles under pressure of about $5 \times 10^3$ psi remains substantially zero, so the particles resist plastic deformation or fracture even at relatively high pressures. The interstitial volume between the particles in the column should preferably be greater than about 45% of the total volume of the column. Particles 22 are preferably porous, the intraparticle pores having mean cross-section dimensions carefully selected to substantially preclude entrance into the pores by the heavyweight compounds that will be processed through the column, but admit into those pores, lightweight compounds that are to be processed simultaneously with the heavyweight compounds. The surfaces of the particles are chromatographically active, either per se as well known in the art, or by treatment with any of the multitude of stationary phase layers well known in the art so as that both the exterior particle surfaces and the internal pore surfaces of the particles are chromatographically active hydrophobic surface exposed to the entire mixture of compounds to be separated.

For example, where such heavyweight compounds to be separated are components of blood plasma (typically albumin plasma protein of mw. approximately 65 kd, immunoglobulins of mw of about 150 kd, and the like), it has been found that pores with cross-section dimensions in the range of about 60 Å will substantially exclude such compounds, i.e. will prevent transit of those compounds into the pores of the particles and therefore restrict chromatographic bonding of those heavyweight compounds primarily to only the very limited external surface area of the particles. In view of the necessarily high reduced velocity to which the mixture containing such heavyweight compounds is subjected, the exposure time of those compounds to the chromatographically active surface areas is also very short, so the extent of loading of the relatively heavyweight compounds on the column particles is extremely limited. Accordingly, as will be apparent from the Examples set out hereinafter, these relatively heavyweight compounds are substantially not trapped and pass through the column in a tight band very quickly.

On the other hand, the lightweight compounds that are intended to be processed simultaneously for separation from the heavyweight compounds, being typically less than 1 kd, can readily access the pores of the chromatographically active particles. Accordingly such smaller molecules tend to be readily trapped on the exterior surface and the much large area of the interior pore surfaces of the particles. It will be understood that the optimum maximum pore cross-section dimensions are therefore determined in accordance with the geometry and the molecular weight of the heavyweight compounds that are expected to be processed.

Accordingly, the apparatus of FIG. 1 includes means, such as pump 24 coupled through column switching valve 25 to the proximal end of column 20, for flowing through at least a major portion of the interstitial volume between particles 22, a fluid mixture (from an appropriate source such as reservoir 26 or loop injector 27 at a reduced velocity that is substantially above 5000. In the embodiment shown, the invention also includes pump 28 for alternatively flowing eluant fluid through valve 25 to column 20 from eluant source 29 to elute from particles 22 such relatively lightweight compounds as may have been chromatographically bound upon passage of the initial flow of the mixture through the column. The flow from pump 28 may be at linear velocities that render the flow through column 20 laminar as will be described hereinafter, but may also be at linear velocities high enough to render the flow turbulent, particularly if one desires to limit band spreading of the eluted solute as an inverse function of the Reynolds number for the eluant flow and a direct function of the diffusion coefficient of the solute in the eluant fluid. These latter considerations provide very quick separation between the possibly several lightweight compounds, with very sharp peaks or high resolution.

The embodiment of FIG. 1 includes means, in the form of detector 30 coupled to the distal end of column 20, for detecting the bands of compounds exiting the column. Typically, the detector is an optical detector, such as an ultra-violet detector of varying wavelength capability, or a mass spectrometer. Means, in the form of diverter valve 32 at the input of detector 30, are provided for directing the flow stream from column 20 to either a waste container (as, for example, for the high molecular weight compounds) or detector 30 (as, for example, for the low molecular weight compounds). Means (not shown) such as an appropriately programmed digital computer and electromechanical relays for operating valves 25 and 32, can be provided for automating operation of the system, and being well-known and well within the capabilities of those skilled in the art, need not be described further here. It will be recognized that with turbulent flow of the eluant fluid through column 20, the various compounds of relatively low molecular weight will be separated chromatographically into separate bands as will appear hereinafter; in such case, detector 30 serves as means for spectrally identifying each of the several relatively lightweight compounds eluted.

The upper limit of the flow rate of liquid into the input of most commercially available mass spectrographs is usually not more than 3 ml/min. Accordingly, it will be apparent that the flow of eluant with the solute of relatively low molecular weight compounds from the distal end of column 20 into the spectrograph should be below about 3 ml/min. In order to clean and equilibrate the fluid lines to prevent carryover from one injection to the next, the apparatus of FIG. 1 includes bypass loop 34 selectively connecting the output from valve 25 to the input to valve 32. This structure enables each of independent pumps 24 and 28 to be operated by selection of valve 25 and 32 while column 20 in not in line, and enhances high productivity and sample processing.

The following are examples illustrative of the principles of the present invention:

EXAMPLE 1

A sample mixture was prepared containing 0.05 g. blue dextran, a large molecular weight compound of mw ~2,000,000, dissolved in 1.0 ml. of water, and two low molecular weight compounds, 100 $\mu$g methyl paraben, and 100 $\mu$g propyl paraben. It will be appreciated that the latter two compounds differ only by one methyl group. This mixture is believed to be representative of a class of separations of enormous interest in drug discovery. Using conventional separation techniques to separate these compounds from one another creates a major problem inasmuch as throughput of samples of this nature has been a major bottleneck in the prior art.

Figure 2:
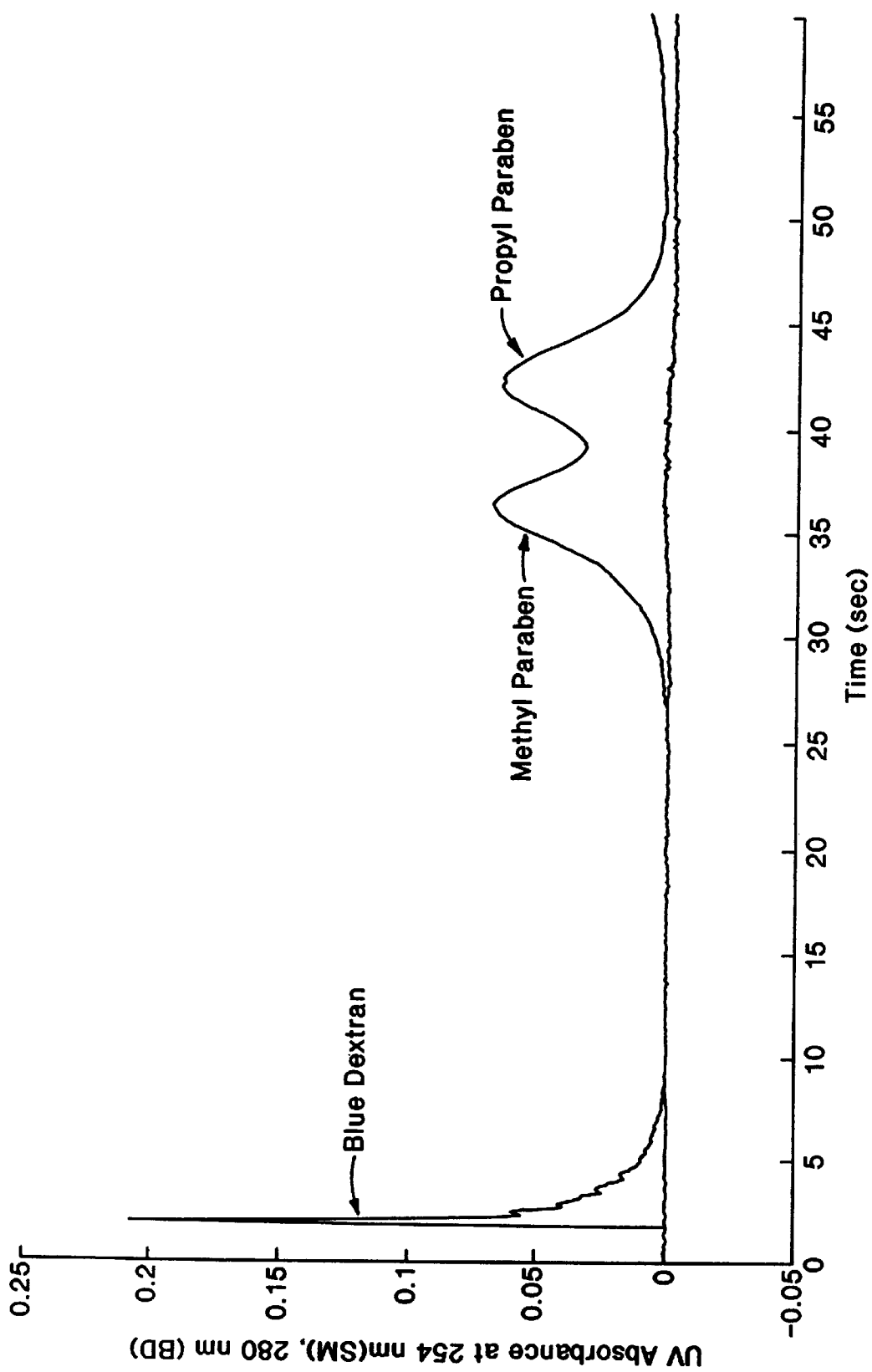
FIG. 2 is a trace of an ultraviolet detector showing a graphical representation in coordinates of absorbance vs. time, of the separation of a compound of relatively large molecular weight from compounds of relatively low molecular weight as described in Example 1.

The sample mixture was introduced into a Model 2300 HTLC system (Cohesive Technologies, Acton, Mass.) having a chromatographic column 20 dimensioned 1 mm×50 mm, and containing packed, porous silica particles of average size 60 $\mu$m, derivatized with a coating of $C_{18}$ to constitute a reverse phase column. The latter exhibited an interstitial volume between the particles of greater than 45% of the total volume of the column, the majority of the channels between the particles having mean cross-section dimensions substantially less than about 5 $\mu$m. The mixture was fed through the column at a reduced velocity substantially greater than about 5,000 (at a flow rate of 10 ml/min) so that the flow was clearly turbulent. As shown in FIG. 2, the large molecular weight compound exited the column first within 10 seconds, and was channeled to a detector (Linear UV VIS Model 205) operating at 280 nm. Commencing at 20 seconds after injection of the sample, the valve was switched and a linear gradient for 0% to 100% acetonitrile over 30 seconds at a flow rate of 0.8 ml/min was run. The smaller molecular weight compound was spectrally identified in the ultra-violet detector at 254 nm, the peaks showing partial separation of the relatively low molecular weight compounds from each other and from the relatively large molecular weight compound, all within less than 50 seconds total analysis time.

EXAMPLE 2

Figure 3:
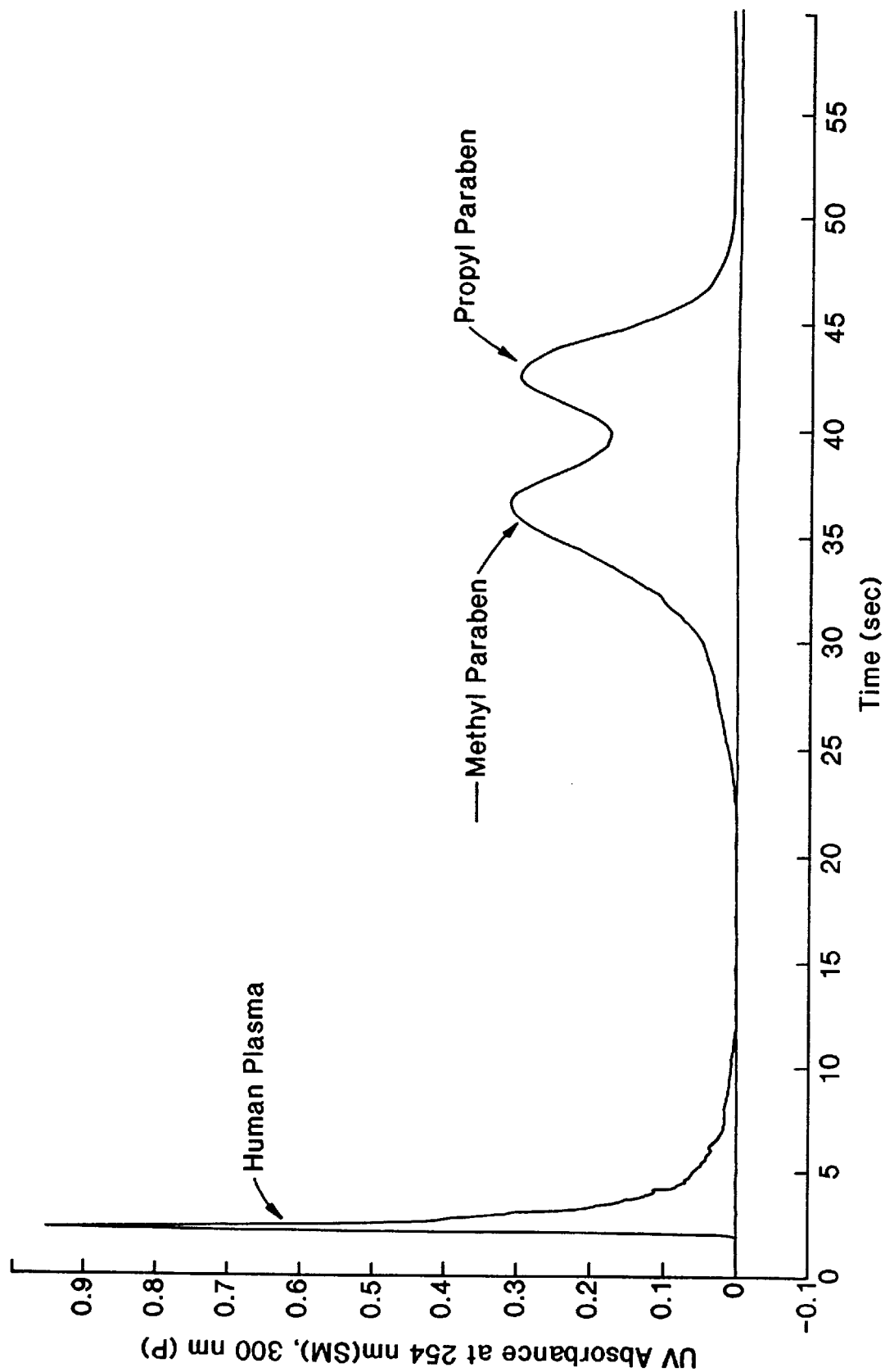
FIG. 3 is a trace of an ultraviolet detector showing a graphical representation in coordinates of absorbance vs. time, of the separation of a compound of relatively high molecular weight from compounds of relatively low molecular weight as described in Example 2.

FIG. 3 shows an ultraviolet detector trace at 280 nm. and 254 nm. of a sample of target molecules of methyl and propyl paraben in human plasma, flowed through the same equipment as in Example 1, at a flow rate of 10 ml/min using 10 mM ammonium acetate aqueous solution as the mobile phase, subsequently eluted with a second mobile phase of acetonitrile. The gradient used was to linearly increase the mobile phase to 100% acetonitrile over 30 seconds. It will be seen that substantially all of the plasma exits the column in less than about 10 seconds and the target lower molecular weight compounds exit in between about 30 to about 50 seconds.

EXAMPLE 3

Figure 4:
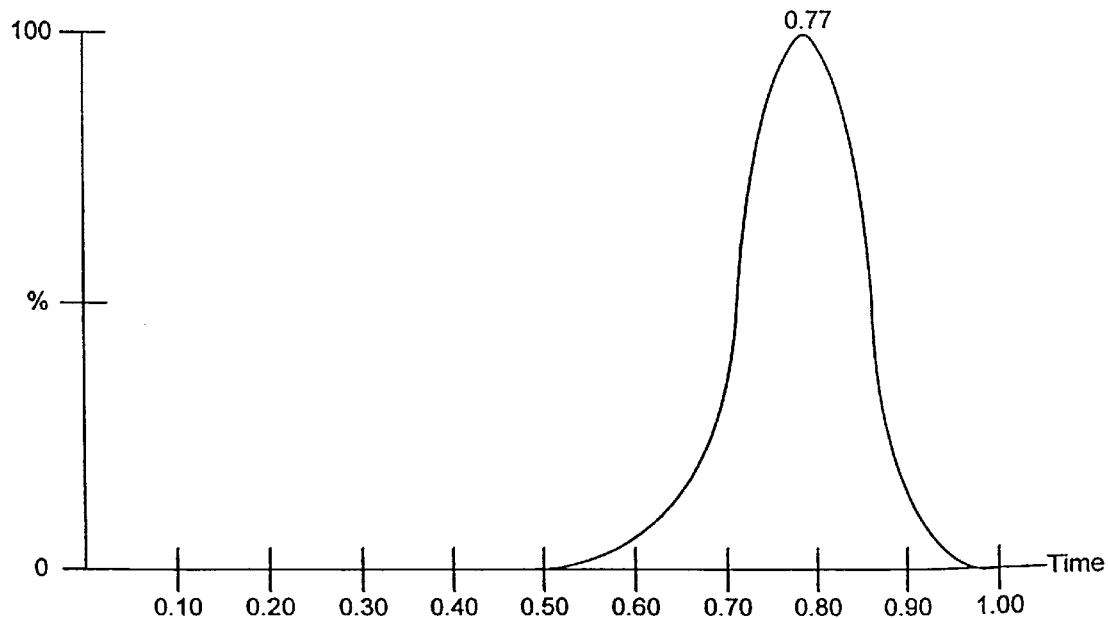
FIG. 4 is a trace of a mass spectrometer detector showing a graphical representation in coordinates of absorbance vs. time, of the separated target molecule after separation from the high molecular weight compound, as described in Example 3.

FIG. 4 shows a mass spectrometer trace of absorbance vs. time for a target molecule of lidocaine. The sample mixture was flowed through the same equipment as in Example 1, at a flow rate of 10 ml/min. The sample mixture contained lidocaine spiked at a concentration of 100 pg/$\mu$l into rabbit plasma. The rabbit plasma was eluted from the column in approximately 10 seconds and channelled to waste. A linear gradient of from 0 to 100% acetonitrile was then run at a flow rate of 1 ml/min and the column effluent directed into a mass spectrometer (Micromass) using a flow splitter that split the flow at a ratio of 2:1. FIG. 4 indicates the output of the mass spectrometer in which the lidocaine was identified as to mass number, eluting within 60 seconds of total analysis time.

Since certain changes may be made in the above described apparatus and process without departing from the scope of the invention herein involved, it is intended that all matter contained in the above description or shown in the accompanying drawing shall be interpreted in an illustrative and not in a limiting sense.

What is claimed is:

1. A method of separating compounds of relatively low molecular weight substantially not greater than about one kilodalton from compounds having relatively high molecular weights substantially an order of magnitude greater or more than said low molecular weight compounds in a liquid mixture of said compounds, said method comprising the steps of flowing said mixture through a chromatographic body formed of a substantially uniformly distributed multiplicity of rigid, solid, porous particles having chromatographically active, hydrophobic exterior and pore surfaces, average diameters of not less than about 30 $\mu$m, and average pore diameters sufficiently small to substantially exclude introduction of said compounds of relatively high molecular weight into said pores, the flow of said mixture being at a velocity sufficient that within at least a substantial portion of the interstitial volume between said particles said flow is at a reduced velocity greater than about 5,000, so that said high molecular weight compounds are swept through said body without substantially binding chromatographically within said pores and exit from said body in a relatively tight band;

after said band of high molecular weight compounds has exited said body, eluting said relatively low molecular weight compounds from said body with an eluant liquid at a reduced velocity less than 5000; and thereafter recovering at the exit of said body the eluted relatively low molecular weight compounds separately from said relatively high molecular weight compounds.

2. A method of separating as set forth iii claim 1 including the step of spectrographically identifying the recovered relatively low molecular weight compounds.

3. A method of separating as set forth hi claim 1 including the step of spectrographically identifying the recovered relatively high molecular weight compounds.

4. A method of separating as set forth in claim 2 or 3 wherein said step of spectrographically identifying is effected by mass-spectroscopy.

5. A method of separating as set forth in claim 2 or 3 wherein said step of spectrographically identifying is effected by ultraviolet absorption.

6. A method of separating as set forth in claim 1 wherein said step of elating said low weight molecular compounds from said body includes the step of flowing said eluant at a substantially lowered flow rate from said body.

7. A method of separating as set forth in claim 6 wherein said lowered flow rate is less than about 3 ml/min.

8. A method of separating as set forth in claim 1 wherein said relatively low molecular weight compounds recovered separately from said relatively high molecular weight compounds are eluted by a liquid eluant from alike body at a flow rate that will effect substantially laminar flow of said eluant through said like body, and thereafter spectrographically identifying the elated low molecular weight compounds.

9. A method of separating as set forth in claim 8 wherein the step of spectrographically identifying is effected with a mass spectrograph.

10. A method of separating as set forth in claim 8 wherein the step of spectrographically identifying is effected by ultraviolet absorption.

* * * * *